(12) United States Patent
Anderson et al.

(10) Patent No.: US 6,361,821 B1
(45) Date of Patent: Mar. 26, 2002

(54) METHOD OF TREATING AN EXHAUST SENSOR AND A PRODUCT THEREOF

(75) Inventors: Conrad H. Anderson, Davison; Kerry J. Gross, New Lothrop; Richard F. Beckmeyer, Davisburg; William J. LaBarge, Bay City, all of MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/737,442

(22) Filed: Dec. 13, 2000

(51) Int. Cl.$^7$ .................................................. B05D 5/12
(52) U.S. Cl. ..................... 427/58; 427/115; 427/123; 427/126.3; 427/352; 427/383.1
(58) Field of Search ................. 427/58, 123, 126.3, 427/115, 383.1, 352; 134/41; 148/23

(56) References Cited

U.S. PATENT DOCUMENTS

| | | |
|---|---|---|
| 3,556,957 A | 1/1971 | Toledo et al. |
| 4,136,000 A | 1/1979 | Davis et al. |
| 4,169,777 A | 10/1979 | Young et al. |
| 4,277,323 A | 7/1981 | Muller et al. |
| 4,426,253 A | 1/1984 | Kreuz et al. |
| 4,940,528 A | 7/1990 | Oki et al. |
| 4,986,880 A | 1/1991 | Dorfman et al. |
| 5,334,284 A | 8/1994 | Ngo |
| 5,384,030 A | 1/1995 | Duce et al. |
| 5,395,506 A | 3/1995 | Duce et al. |
| 5,433,830 A | 7/1995 | Kawai et al. |
| 5,467,636 A | 11/1995 | Thompson et al. |
| 5,602,325 A | 2/1997 | McClanahan |
| 5,616,825 A | 4/1997 | Achey et al. |
| 5,733,504 A | 3/1998 | Paulus et al. |

*Primary Examiner*—Brian K. Talbot
(74) *Attorney, Agent, or Firm*—Vincent A. Cichosz (57) ABSTRACT

The sensor is formed by disposing an electrolyte between and in intimate contact with a first electrode on the one side and a second electrode on the other side to form an assembly, heating the assembly, treating the assembly with an alkaline solution and removing the impurities to obtain optimal sensor performance. Alternatively, an electrolyte is formed, sintered, treated with alkaline solution, and then the electrodes are applied.

21 Claims, 5 Drawing Sheets

METHOD OF TREATING AN EXHAUST SENSOR AND A PRODUCT THEREOF

TECHNICAL FIELD

The invention relates generally to exhaust sensors. Particularly, the present invention relates to a method of treating an electrolyte and of forming an exhaust sensor.

BACKGROUND

The automotive industry has used exhaust sensors in automotive vehicles for many years to sense the composition of exhaust gases, e.g., oxygen, hydrocarbons, and nitrous oxides. For example, sensors are used to determine the exhaust gas content for alteration and optimization of the air to fuel ratio for combustion.

A sensor typically has a conductive solid electrolyte disposed between porous electrodes. In the use of a sensor for automotive exhaust, the unknown gas is exhaust and the known gas (i.e., reference gas) is usually atmospheric air because oxygen content in the air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force (emf) is developed between the electrodes according to the Nerst equation:

$$E = \left(\frac{RT}{4F}\right)\ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas A sensor comprises an electrolyte disposed between a sensing electrode and a reference electrode. The electrolyte typically comprises any material conventionally employed for sensor electrolytes, including but not limited to, zirconia, such as yttria doped zirconia, ceria, strontium cerium oxide, barium cerium oxide, strontium cerium zirconates, and the like, and mixtures thereof. The electrodes on the other hand, typically comprise metals such as platinum, gold, palladium, rhodium, iridium, osmium, ruthenium, and mixtures and alloys comprising at least one of the foregoing, and other metals. Combined with the metals are metal oxides such as ceria, calcia, yttria, magnesia, lanthana, and mixtures and alloys comprising at least one of the foregoing.

A sensor is typically formed by disposing an electrolyte between and in intimate contact with a pair of electrodes such as a sensing electrode and a reference electrode to form an assembly. This assembly is then fired to a certain temperature as part of the forming process. During firing, certain impurities such as silica, sodium, and the like, accumulate on the surface of the electrolyte and the electrodes. These impurities affect the overall performance of a sensor. In particular, the surface composition of the electrolyte and the electrode are affected causing poor sensor performance.

With conventional sensor formulations, the desired surface composition is often not attained due to impurities introduced during the firing process at very high temperatures. Therefore, to remove the impurities, several methods have been used to treat the surface of the electrolyte and the electrode. Some of the treating methods include ion milling, electrical aging, hydrogen fluoride (HF) etching, and the like.

For example, ion milling a conical sensor is not very effective because only the outer surface of the sensor can be reached leaving the interior of the sensor untreated. The untreated area may retain impurities causing a low surface composition. Similarly, ion milling other sensors such as a flat plate sensor or a wide range sensor is not practical because of erosion of the porous protective layer on the outer surface.

With the electrical aging treatment method, the treatment advantageously changes the electrical properties of the electrode, however, impurities continue to exist on the electrodes, resulting in poor sensor performance. Essentially, electrical aging affects the boundary layer between the platinum electrode and the ionically conductive zirconia body. Poor "connections" between the platinum electrodes and the yttria-zirconia electrolyte inhibit oxygen ions from efficiently entering into (inner electrode) and coming out of (outer electrode) the yttria-zirconia electrolyte. The rate of oxygen ion transport is important to the functioning of the sensor. High voltage minimum indicates not enough oxygen ions formed or transferred to the yttria-zirconia from the inner electrode, while low voltage maximum indicates the oxygen ions are not being used effectively at the outer electrode.

As the electrode is electrically aged the charge causes cationic impurities such as sodium to migrate towards the (−) pole. The anionic impurities such as chlorine are migrated towards the (+) pole. Alternating current drives both anions and cations towards both the surface and the boundary layer. The zirconium oxide at the boundary layer can break its bonds to platinum and be converted to non-ionically conductive materials such as zirconium oxychloride or sodium zirconium oxide. The yttrium can be converted to yttrium chloride the platinum surface can be converted to platinum chloride.

Hydrogen fluoride etching is capable of removing some surface impurities primarily metal oxides such as silica, alumina, yttria, and zirconia, capable of dissolving both metals and metal oxides. However, the rate of dissolution for metal oxides is orders of magnitude faster than for metals. For example, XPS of some poisoned samples detected the metals copper, silver, indium and lead present in the platinum sputtered electrode. A 2-wt % hydrogen fluoride treatment for 15 seconds was applied to 50 sensors. The hydrogen fluoride solution was evaporated and residue analyzed. The oxides of silica, alumina, yttria and zirconia were detected, while the metals copper, silver, indium and lead were not detected. The same sensors were hydrogen fluoride treated several times for different lengths of time. Eventually the platinum electrode completely de-bonded and the sensor was no longer functional. XPS analysis of the de-bonded platinum showed the metallic impurities still present. Consequently, either the impurities are not removed from all sensor areas or a portion of the sensor can be damaged due to excessive etching.

There exists a need in the art for treating an oxygen sensor that can reduce material and process impurities, and which will help provide a desired electrode surface composition and electrolyte surface composition to attain optimal sensor performance.

SUMMARY

The above-discussed issues and deficiencies are overcome with the methods of forming a sensor. In one embodiment a sensor is formed by forming an electrolyte. The electrolyte is densified and exposed to an alkaline solution comprising potassium hydroxide and/or barium hydroxide. An assembly is formed by disposing the electrolyte between and in intimate contact with a first electrode and a second electrode.

In another embodiment, the sensor can be formed by disposing an electrolyte between an in intimate contact with a first electrode and a second electrode to form an assembly. The assembly is heated and exposing to an alkaline solution. In this embodiment, the first electrode comprises up to about 5 wt % rhodium and up to about 99.5 wt % platinum, based upon the weight of the electrode.

BRIEF DESCRIPTION OF THE DRAWINGS

Refer now to the Figures, which are meant to be exemplary, not limiting, and wherein like elements are numbered alike.

DESCRIPTION OF THE INVENTION

The method of forming an exhaust sensor can comprise one or more electrochemical cells disposed within dielectric support layers. Each electrochemical cell comprises an electrolyte, porous or solid, disposed in a dielectric substrate, and in between a first electrode and a second electrode, with adjacent cells optionally sharing an electrode. On the external surface of the sensor is typically a dielectric layer with a porous protective material disposed in the layer, opposite the first (outer) electrode of one of the cell(s). On the opposite side of the cell(s) can be a heater and/or other conventional components. Disposed in electrical communication with the electrodes and heater are leads connecting the electrodes and heater to an external load through vias disposed in an end of the layers opposite the electrochemical cell(s). Other optional sensor components include a lead gettering layer, reference gas storage area, a reference gas access passageway to an internal electrode, and a protective coating which may be disposed on the external surface of the sensor.

The various sensor components, electrolyte, electrodes, and others such as leads, contacts, heater(s), substrates, ground plane(s), lead gettering layer(d), protective coating, etc., can comprise materials conventionally employed in that type of sensor. For example, the heater and ground plane can comprise a metal, such as platinum, palladium, and the like; metal oxides such as alumina, and the like; as well as alloys and mixtures comprising at least one of these materials. The protective coating, which is often applied by dipping, spraying, or the like, typically comprises a metal oxide, such as alumina, alone or in combination with one or more alkali or alkaline earth metals.

As is conventional, the electrolyte any material typically employed as sensor electrolytes, including, but not limited to, zirconia which may optionally be stabilized with calcium, barium, yttrium, aluminum, lanthanum, cesium, gadolinium, and the like, as well as combinations comprising at least one of the foregoing. For example, the electrolyte can be alumina and yttrium stabilized zirconia. Unlike conventional electrolytes, however, the raw materials employed herein do not require a high degree of purity to attain optimal sensor performance (e.g., an impurity of about 1,000 to about 2,000 parts per million is acceptable, while conventional sensors require an impurity of less than 1,000 ppm).

The electrodes, which should be stable in the sensor environment, typically comprise a metal and/or a metal oxide. Possible electrode materials include metals such as platinum, gold, palladium, rhodium, iridium, osmium, ruthenium, and other metals; metal oxides, such as ceria, zirconia, calcia, yttria, magnesia, lanthana, and the like; and mixtures and alloys comprising at least one of the foregoing materials.

The specific composition of the electrolyte is preferably chosen to optimize sensor performance. During sensor formation, namely firing, however, the composition of the electrolyte changes on its surface due to impurities. That is, impurities in the composition migrate to the electrolyte surface. As a result, a less than desirable surface composition is obtained. Maintaining a desired surface composition will enhance sensor performance. For example, an electrolyte comprising about 10 parts zirconia, 1 part yttria and 1 part alumina before firing may have a ratio of 10 parts zirconia, 2.5 parts yttria, 4 parts alumina, 6 parts silica and 2 parts sodium on the surface after firing. This equates to a $^{10}/_{24}$ zirconia surface composition, while the desired surface composition is $^{10}/_{12}$. Similarly, for example, an electrode comprising 10 parts platinum and 10 parts zirconia before firing may have a ratio of 6 parts platinum, 10 parts zirconia, 1.5 parts yttria, 1.5 parts alumina, 5 parts silica and 1 part sodium on the surface after firing. This equates to a $^{6}/_{25}$ electrode surface composition, while the desired surface composition is $^{10}/_{25}$.

In order to maintain the desired composition at the electrode and electrolyte surface, the fired electrolyte or fired sensor is cleaned with a fluxing solution, namely an alkaline solution. Possible fluxing solutions include those capable of removing the impurities at a substantially equal rate from each sensor component. In other words, unlike hydrogen fluoride, an etching solution which has different reaction rates with zirconia, yttria, alumina, silica, etc., the fluxing solution preferably has substantially equal reaction rates with each compound in the electrolyte, or the electrolyte and electrode so that impurities can be removed from the surface without again changing the composition of the surface away from the desired composition.

A metal hydroxide flux, for example, is a metal hydroxide heated to its melting point. Metal hydroxide fluxes dissolve most ceramics and metal oxides at essentially the same rate. In one embodiment using a platinum electrode and yttria-zirconia electrolyte, only the platinum avoids dissolution, leaving a small residual amount of metal hydroxide over the surface of the electrode. When the metal hydroxide is melted it dissolves everything except the platinum, the entire exposed yttria-zirconia surface and impurities on the platinum surface are dissolved. After fluxing, the exposed yttria zirconia surface is the yttria-zirconia that was about 2 to about 5 nanometers below the surface prior to fluxing. The exposed platinum is pure platinum with no metal contaminates (e.g., less than 0.5% contaminants).

Some possible fluxing solutions (no water rinse before drying and calcining) include hydroxides such as lanthanum hydroxide, lithium hydroxide, sodium hydroxide, cesium hydroxide, magnesium hydroxide, calcium hydroxide, strontium hydroxide, and the like; oxides such as potassium oxide, sodium oxide, barium oxide, and the like; barium solutions such as barium zirconium isopropoxide (BaZr $(OC_3H_{7i})_6$), barium isopropoxide ($Ba(OC_3H_{7i})_2$) in isopropanol solution, barium ethoxide ($Ba(OC_2H_5)_2$) in ethanol barium methoxyethoxide ($Ba(OCH_2CH_2OCH_3)_2$) in 2-methoxyethanol, and the like; alkoxides (e.g., methoxide, ethoxide, isopropoxide, and the like), such as lanthanum alkoxide, potassium alkoxide, sodium alkoxide, magnesium alkoxide, calcium alkoxide, strontium alkoxide and the like; as well as combinations comprising at least one of the foregoing solutions. Additional fluxing solutions comprise those described above, wherein the metal is lanthanum, potassium, lithium, sodium, magnesium, calcium, strontium, yttrium, zirconium, and the like, as well as combinations comprising at least one of the fluxing solutions.

The concentration of the alkaline solution should be sufficient to remove the impurities. For example, a solution of potassium hydroxide can have any concentration which will not adversely effect the sensor components with a concentration of below about 0.3 molar (M) preferred, below about 0.1 M more preferred, and below about 0.05 M especially preferred.

Cleaning of the electrolyte or sensor with the alkaline solution can be accomplished using conventional techniques such as spraying, dipping, and the like, with immersion of the electrolyte or sensor for a sufficient period of time to remove greater than about 50% of the impurities from the electrolyte, or electrolyte and electrode surface preferred, with sufficient time to remove greater than about 75% of the impurities more preferred, and sufficient time to remove greater than about 90% or even 99% or greater especially preferred. Typically up to about 5 minutes, or so, immersion can be employed, with up to about 2 minutes preferred, and up to about 1 minute especially preferred. Further enhancement of impurity removal can be obtained via agitation of the alkaline solution, e.g., via bubbling an inert gas through the solution, boiling, stirring, vibrating, and combinations comprising at least one of these techniques, and the like.

A sensor as described above is formed by providing a first electrode and a second electrode, and disposing an electrolyte in between and in intimate contact with the first electrode and the second electrode to form an assembly. After the assembly has been heat treated (i.e., co-fired), it is then exposed to an alkaline solution to remove up to or exceeding 99% of the contaminants. This assembly can then optionally be rinsed with water or deionized water, dried, and calcined.

Alternatively, a sensor can be formed comprising the electrolyte described herein by first forming the cleaned electrolyte. Namely, the electrolyte is formed into the desired size and shape as is conventional. It is then densified by exposing it to sintering temperatures, typically temperatures up to about 1,800° C. or so, with temperatures of about 1,400° C. to about 1,600° C. preferred for a period sufficient to attain at least about 85% densification, with about 93% or greater preferred (e.g., for a period of up to about 240 minutes, with about 60 minutes to about 180 minutes preferred). The densified electrolyte is then treated with the fluxing solution prior to the application of electrodes or opposite side thereof. The electrodes can be applied via any conventional technique such as sputtering, vapor deposition, ink application, or the like. Over the outer electrode, a protective layer is typically applied in a conventional fashion, such as flame spraying, dipping, vapor deposition, or the like. Conventional components can then be included, such as disposing a heater in thermal communication with the inner electrode, placing the sensor in a protective housing (e.g., conical shell with a seal such as a talc pack).

For example, a sensor comprising an electrolyte composition of about 10 parts zirconia, about 1 part yttria and about 1 part alumina (i.e., a zirconia ratio of about $10/12$) can be formed into a conical shape and sintered at about 1,500° C. Electrodes, having a composition of 10 parts platinum and 10 parts zirconia (i.e., a platinum ratio of about $10/20$) can then be sputtered onto each side of the electrolyte. Once the electrolyte is cooled, it is immersed in a 0.002M solution of boiling potassium hydroxide for 1 minute. The sensor can then, optionally, be washed with water (e.g., deionized water), or the like, and dried. A heater can then be disposed within the cone and connected to contact pads via leads, and a protective layer can be disposed over the outer electrode to form the sensor. The resultant sensor not only comprises the above overall desired composition, but the surface of the electrolyte comprises a zirconia ratio of about $10/12$.

To facilitate introduction of the alkaline solution to the electrolyte, the solution may contain alcohol, so as to produce an about 0.01 N to about 1.0 N solution, with an about 0.05N to about 0.5N solution preferred, and an about 0.075N to about 0.25N especially preferred. Some possible alcohols include ethanol, isopropanol, and the like, as well as combinations comprising at least one of the foregoing alcohols.

Figure 1:
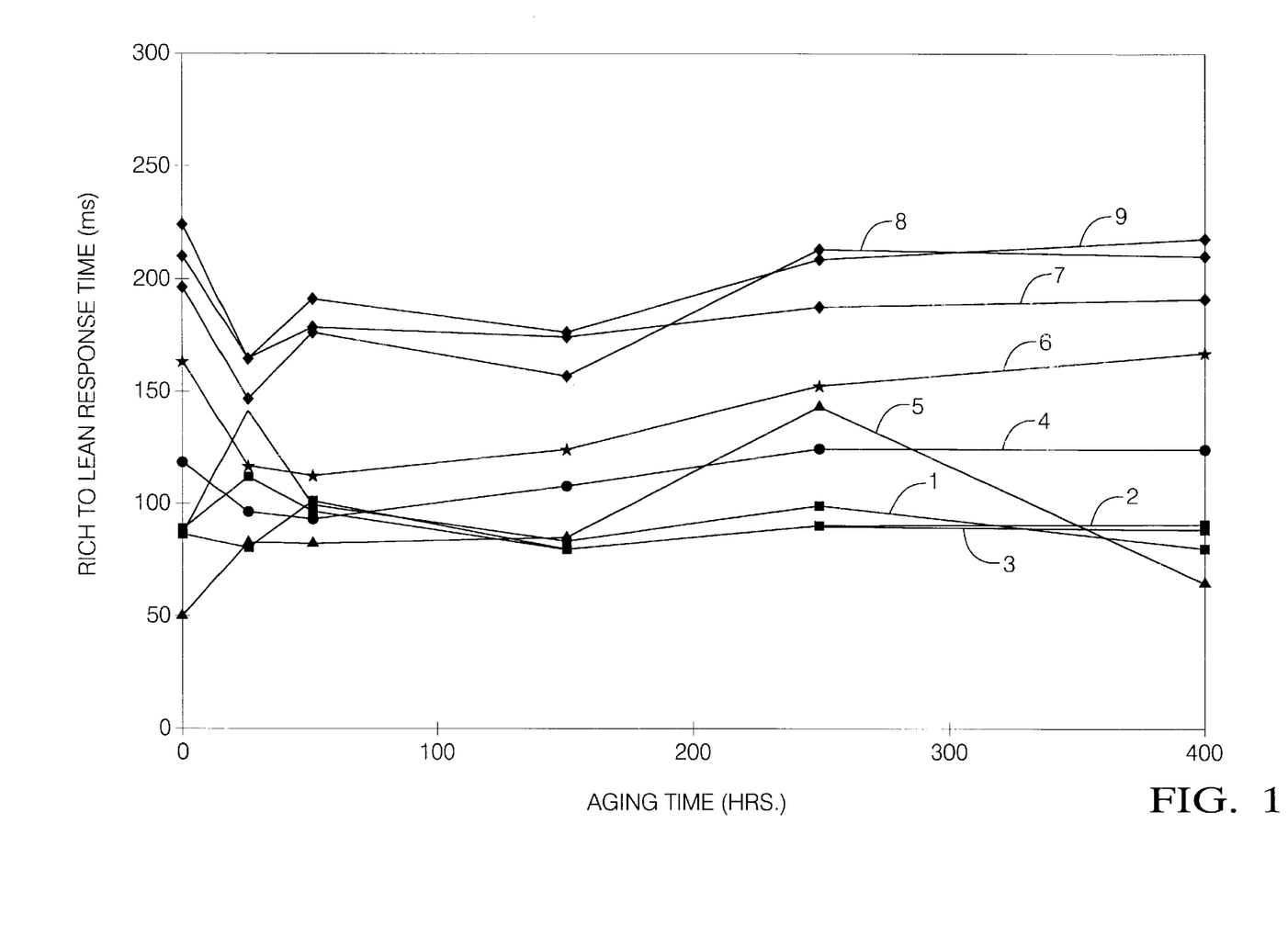
FIG. 1 is a graphical representation illustrating rich to lean response time versus aging time for one embodiment over standard sensors at ½ Hertz (Hz) and at 260° C.
Figure 2:
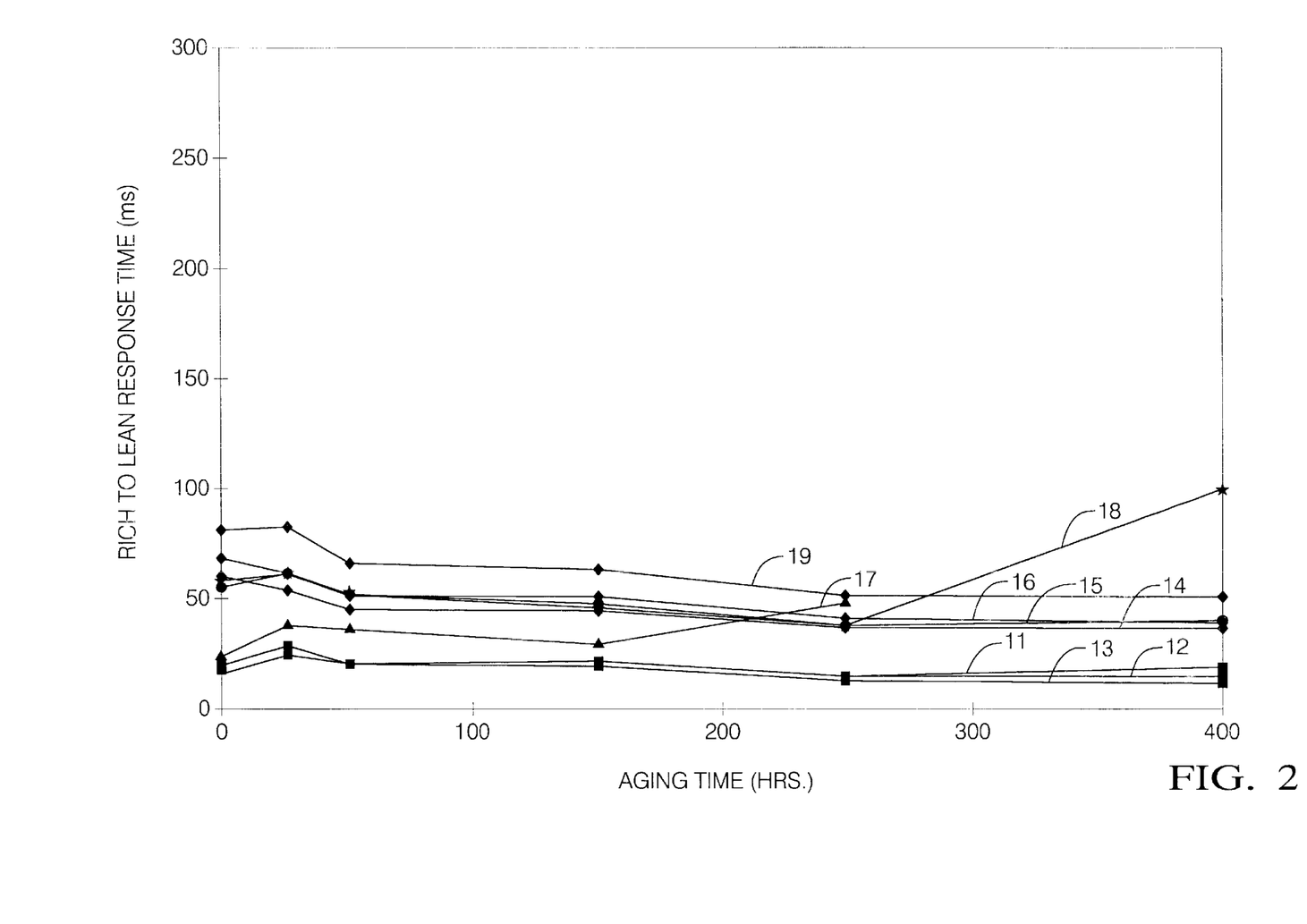
FIG. 2 is a graphical representation illustrating rich to lean response time versus aging time for one embodiment over prior art sensors at 2 Hertz (Hz) and at 595° C.

The result of forming sensors using the alkaline solution described herein is illustrated in FIGS. 1 through 5. FIGS. 1 and 2 show comparisons of rich to lean (RL) response times obtained from treated and untreated sensors at 260° C. and 595° C. respectively. Lines 1, 2, and 3 in FIG. 1 and lines 11, 12, and 13 in FIG. 2 are sensors cleaned with a potassium hydroxide solution. The treated sensors (i.e., sensors having treated electrolytes) were compared with untreated sensors (electroplated, lines 4 and 15; sputtered conical, lines 5 and 17; inexpensive post converter sensor, lines 6 and 18; and co-fired electrodes, conical, lines 7, 8, 9, 14, 16, and 19) in FIGS. 1 and 2. As can be seen from FIGS. 1 and 2, the co-fired sensors cleaned with alkaline solution (lines 1–3 and 11–13) generally attain better response time than the sensors having pure platinum electrodes (i.e., electroplated electrodes applied after the yttria-zirconia body was fired, lines 4, 6, and 18, and those which had sputtered electrodes, lines 5 and 17).

The treated sensors, lines 1, 2, and 3 establish a faster response time (about 80 milliseconds (ms) over a 400 hour period than untreated sensors which typically show response times exceeding about 100 ms, and even greater than 150 ms. for those characterized at 595° C., the treated sensors maintained a substantially consistent response time below about 25 ms (lines 11, 12, and 13), while the other sensors response times were about 50 ms or greater.

Figure 3:
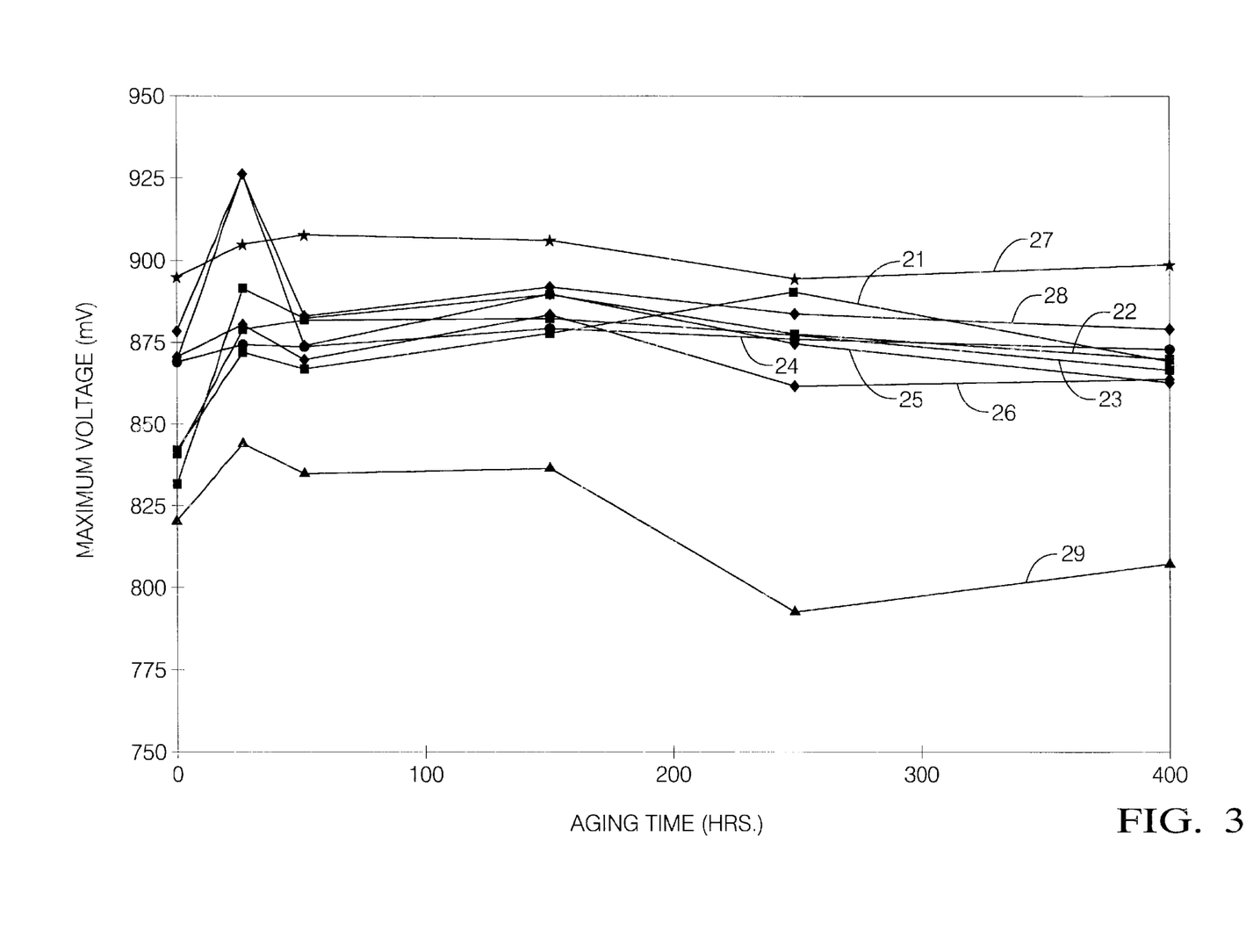
FIG. 3 is a graphical representation of maximum voltage versus ageing time for one embodiment over prior art sensors at ½ Hertz (Hz) and at 260° C.
Figure 4:
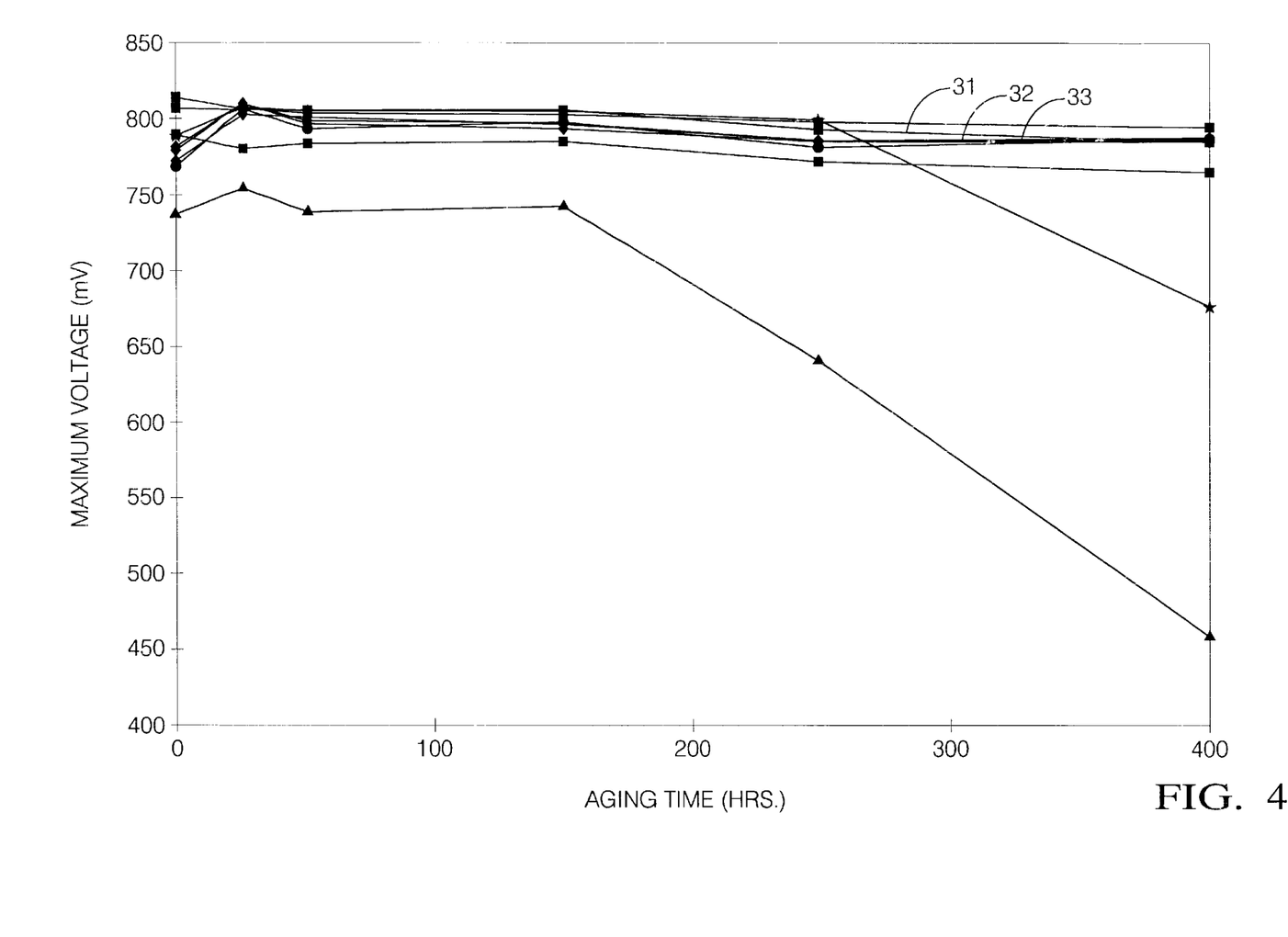
FIG. 4 is a graphical representation of maximum voltage versus ageing time for one embodiment over prior art sensors at 2 Hertz (Hz) and at 595° C.
Figure 5:
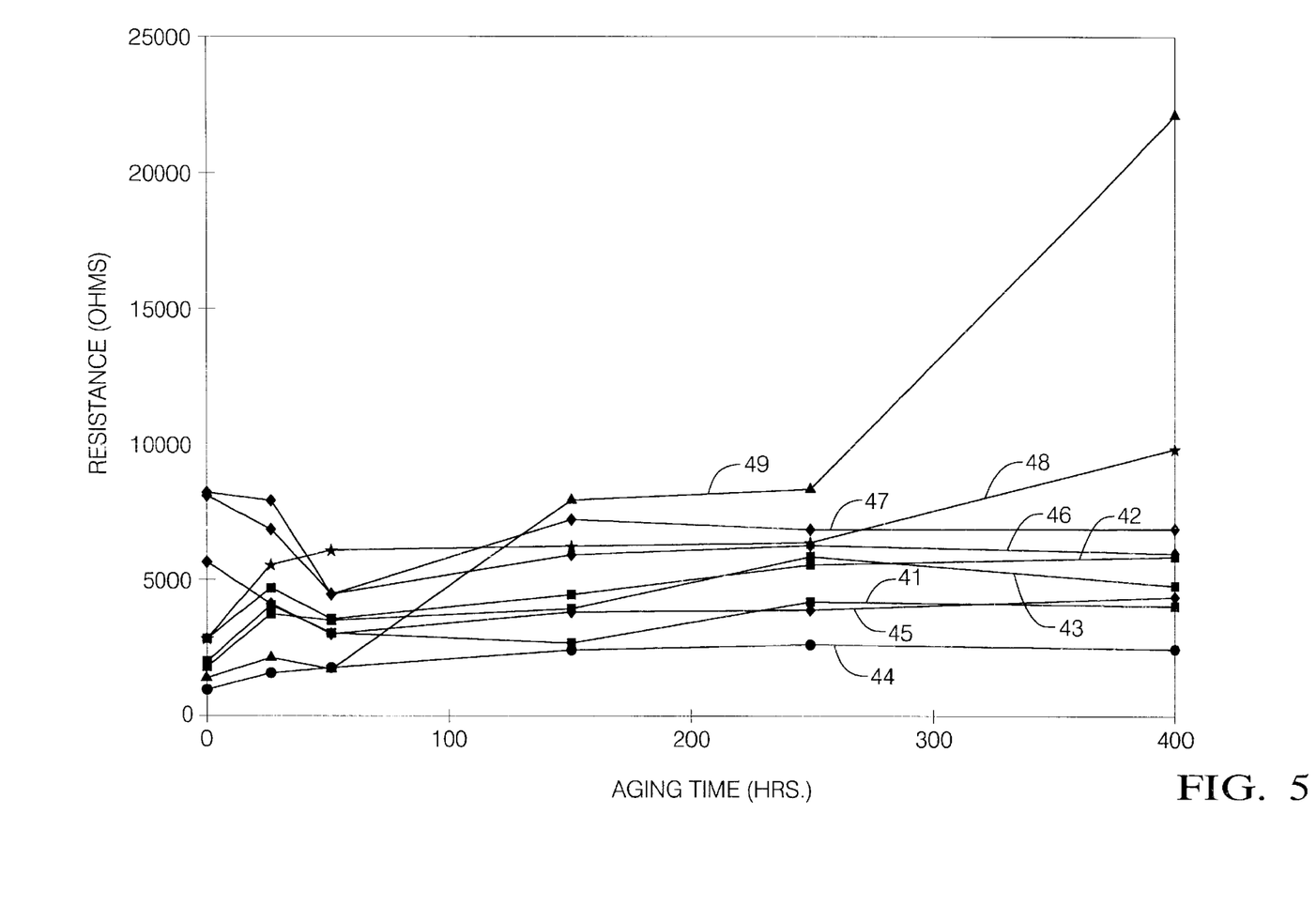
FIG. 5 is a graphical representation of resistance versus ageing time for one embodiment versus prior art sensors at ½ Hertz (Hz) and at 260° C.

FIGS. 3 and 4 show comparisons of voltage in a treated sensor and an untreated sensor. The treated sensor comprised a sensor with a flame sprayed spinal porous protective material and an alumina protective coating. The sensor was treated in 0.005 M potassium hydroxide. Samples from a treated sensor, lines 21, 22, and 23 in FIG. 3 and lines 31, 32, and 33 in FIG. 4, reflect a substantially consistent voltage over a 400 hour period of about 870 millivolts (mV) at 260° C. and 0.5 hertz (Hz), and about 800 mV at 595° C. and 0.5 Hz. In contrast, untreated sensors exhibited varying voltage. FIG. 5, is a graph showing the improved resistance of the treated sensor, lines 41, 42, and 43, over the untreated sensor, lines 44, 45, 46, 47, 48, and 49. The treated sensor, lines 41, 42, and 43, showed lower resistance.

In one embodiment, during use, the treated sensor is typically disposed in the stream to be sensed, e.g., the exhaust stream. Based upon the condition of the stream, i.e. rich or lean, oxygen is pumped in or out of the sensor by the pumping cell. The increase/decrease, accordingly, creates an oxygen partial pressure difference between the oxygen at the sensing electrode and at the reference electrode, thereby developing an electromotive force.

The following example is provided to further illustrate the present invention and not to limit the generally broad scope hereof.

EXAMPLES

Example 1

The following process can be used to clean a electrolyte.

A fully fired conical electrolyte is immersed in a beaker containing 0.01M BaOH/ethanol solution. The beaker is placed in an ultrasonic bath for 1 minute. The sensor is removed and air-dried. The cleaned electrolyte is sputtered with platinum. A porous protective layer of spinel is either flame sprayed or plasma sprayed. Then, a drop of alumina slurry is placed on the porous protective layer. The sensor is heated to 700° C. for 15 minutes. The sensor element is then built into a sensor package, with heater leads, element leads etc.

A pure platinum electrode cannot "free" the oxygen from NOx. Thus a pure Pt containing electrode cannot switch at 0.00 delta AF (air/fuel ratio) The switching point is typically about 0.23 delta A/F units. A very clean engine with a pure platinum sensor, lean shifted by about 0.23 delta A/F units emits about 0.122 mg/mile (milligrams per mile) NOx. Federal regulations for ULEV vehicles mandate NOx emissions no more than 0.04 mg/mile.

Rhodium can convert NOx to $N_2$ "freeing" the oxygen for reaction with hydrocarbons. However a rhodium only electrode functions very poorly in most other characteristics. Sputtered platinum electrodes with sputtered rhodium deposited over the platinum are very poor sensors because the exhaust gasses react on only the outermost rhodium layer. Platinum and Rhodium cannot be plated together because all the rhodium plates out before any of the platinum plates out. When platinum and rhodium are co-fired the rhodium dissolves into the bulk and the electrode surface is primarily platinum. Rhodium fluxes the platinum yielding very dense electrodes.

A mixture (containing 92.1 weight percent (wt %) Pt and 1.9 wt % Rh) is combined with 6 wt % (based upon the total weight of the ink) SCFA 100 alumina (i.e., a high purity gamma alumina with a surface area of about 100 $m^2/g$ commonly available from Condea Vista) to form an ink. The ink is applied to a green electrode by screen-printing support layers and a heater are disposed on one side of the electrolyte and a protective layer on the other to form a sensor which is co-fired to temperature up to 1,800° C. for up to 4 hours. The co-fired sensor is immersed in a 0.1 M KOH solution, not rinsed, and fired to about 800° C. for 15 minutes. The KOH fluxes the alumina to potassium aluminate. The alumina no longer "sticks" to the electrode layer or yttria-zirconia and is effectively removed. There are now many holes and much porosity in the fired electrode. Rhodium is exposed at the surface by the fluxing. A sensor produced by this method has a lean shift of about 0.07 delta A/F units. The NOx emissions of a vehicle with a sensor produced by this method are about 0.022 mg/mile. The vehicle is now a ULEV vehicle without any additional equipment or catalysts or EGR systems etc. Consequently, for a planar sensor, a preferred electrode formulation comprises up to about 5 wt % rhodium and up to about 99.5 wt % platinum, with about 0.5 wt % to about 3 wt % rhodium preferred and about 97 wt % to about 99.5 wt % preferred, based upon the total weight of rhodium and platinum. This formulation further preferably comprises up to about 10 wt % alumina, with about 1 wt % to about 6 wt % alumina more preferred, based upon the total weight of the composition.

Example 2

A fully fired wide range sensor (flat element with co-fired porous protect layer) element is immersed in a beaker containing 0.01 M KOH/ethanol solution. The beaker is placed in an ultrasonic bath for 1 minute. This helps the solution pass through the dense porous layer and allows the air in the electrode chamber to escape. The sensor is removed and air-dried. A drop of alumina slurry is placed on the porous protective layer. The sensor is heated to 700° C. for 15 minutes. The sensor element is then built into a sensor package, with heater leads, element leads etc.

Example 3

4,950 grams Condea Vista SCFA-140 Ba, 4,950 grams Cerelox alpha alumina, 9,600 grams water, and 100 grams barium hydroxide are added to a container. The mixture is high shear mixed for about 20 minutes. A conical sensor (with sputtered platinum electrode and plasma sprayed spinel porous protective layer) tip is immersed in the slurry for about 2 seconds. The sensor tip is removed from the slurry. The sensor is placed in a drying oven at 80° C. for 15 minutes. The sensor is removed and placed in a box furnace and calcined at 700° C. for 15 minutes. The resultant sensor had a RL time of 63 ms and no silica poisoning at 100 hours.

Example 4

A poison trap layer was deposited from a slurry of 45 wt % gamma alumina, 45 wt % alpha alumina and 10-wt % alumina from colloidal alumina, in a 0.65 M KOH solution. The sensor with trap layer was calcined at 700° C. The sensor failed silica poisoning tests after about 12 hours. It is believed that the potassium hydroxide concentration was too high. Consequently, a concentration less than about 0.65 M is preferred.

Example 5

A poison trap layer was deposited from a slurry of 45 wt % gamma alumina, 45 wt % alpha alumina and 10 wt % alumina from colloidal alumina, in a 0.12 M KOH solution. Two processes were employed: (1) the alkaline solution was applied, the sensor was heated to 700° C., then apply gamma alumina was applied and the sensor was heated to 700° C. again, and (2) an alkaline gamma alumina slurry was applied and the sensor was then heated to 700° C. The sensor with trap layer was calcined at 700° C. The sensor survived silica poisoning tests for up to about 136 hours.

Example 6

XPS of a sensor electrode showed as expected desired Pt, Zr, Y and undesired Si, Al, Na. The sensor was dipped in a solution containing 10 g barium ethoxide brought to 100 ml volume with ethanol. The sensor was soaked for about 15 minutes. The sensor was not rinsed. The sensor was heated to about 700° C. for about 15 minutes. The sensor is then rinsed with a 50% water and 50% ethanol mixture. Post XPS analysis detected no residual poisons, only as expected Pt, Zr, Y and trace Ba. The Si, Al and Na contaminants were effectively removed.

This method, which can be employed to produce any type of sensor; planar, conical, flat plate, wide range, and the like, overcomes shortcomings that exist in the prior art. Impurities accumulated during manufacturing, especially firing, which result in high electrode/electrolyte interfacial impedance, can be eliminated via treatment with the alkaline solution, leaving the electrodes and the electrolyte with the desired surface composition and a low interfacial impedance. Specifically, the impedances were as follows: treated conical sensor about 80 ohms, treated conical electrolyte then sputtered about 40 ohms, untreated conical about 1200 ohms, and etched conical about 300 ohms. Consistently attaining the desired surface composition enables a consistent sensor performance.

Some of the other advantages to this treatment include reduction and elimination of sensor changes, also known as the "green effect", which occur during the early stages of use; larger production tolerances because poisons left behind during the post process stage are removed by the alkaline solution treatment; elimination of impurities at the post process stage without incurring additional time and labor to the manufacturer; the ability to employ less expensive raw materials while still obtaining optimal sensor performance; and the elimination of lead oxide treatment of the electrodes since this treatment greatly reduces carbon monoxide adsorption on the electrode(s).

Another advantage obtained from our alkaline solution is faster Rich to Lean times. Changing the protective coating slurry from acidic to basic shifts the catalysis from a good steam reforming formulation to a good water gas shift formulation. Steam reforming reacts steam ($H_2O$) and hydrocarbon (HC) over alumina ($Al_2O_3$) making hydrogen ($H_2$), carbon monoxide (CO) and carbon dioxide ($CO_2$). For untreated electrodes with an acidic based alumina coating, the increased CO leads to increased rich to lean times. Potassium or barium basic alumina decreases the amount of CO reaching the electrode. If the electrode has not been treated with alkaline solution the CO that reaches the platinum electrode still binds very tightly and is hard to remove. If soluble alkaline solution has treated the electrode the CO binding to the electrode is greatly reduced and the rich to lean times are significantly reduced. This is substantiated by the Table of a 2.3 Liter Oldsmobile L-4 engine with sensors at 260° C. at 0.5 Hz.

TABLE

| Electrode Type | Lead Treatment | Alkaline Treatment | Protective Coating with Alkaline | RL(ms) |
|---|---|---|---|---|
| Sputtered | Y | N | N | about 75 |
| Sputtered | N | N | N | about 175 |
| Sputtered[1] | Y | Y | N | about 50 |
| plated[2] | — | — | — | about 130 |
| co-fired | N | N | N | about 120 |
| co-fired | N | Y | N | about 55 |
| co-fired | N | N | Y | about 65 |

[1]alkaline treatment to yttria zirconia body, platinum sputtered, and then Pb deposition.
[2]purchased; unknown treatment As is evident from the Table, treatment with a protective coating containing alkaline solution obtains a better rich to lean (RL) response time; i.e., below about 65 milliseconds (ms), with below about 60 ms preferred, and about 55 or lower especially preferred. The co-fired sensor with the alkaline treated electrode attained greater than a 10% improvement in RL response time over the lead treated, sputtered electrode, with greater than 25% improvement attained with an alkaline solution treatment. Compared to untreated, co-fired electrodes, the improvement is at least 45%.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claimed is:

1. A method of forming a sensor, comprising:
   forming an electrolyte;
   densifying the electrolyte;
   exposing the electrolyte to an alkaline solution selected from a group consisting of potassium hydroxide and barium hydroxide; and
   disposing the electrolyte between and in intimate contact with a first electrode and a second electrode to form an assembly.

2. The method of claim 1, wherein said potassium hydroxide concentration comprises below about 0.3 molar in water.

3. The method of claim 1, wherein said potassium hydroxide concentration comprises below about 0.1 molar in water.

4. The method of claim 1, wherein said potassium hydroxide concentration comprises below about 0.05 molar in water.

5. The method of claim 1, wherein said assembly is treated by immersing said assembly in an alkaline solution.

6. The method of claim 5, further comprising, coating at least a portion of the assembly with a protective coating.

7. The method of claim 5, wherein said assembly is immersed in boiling alkaline solution.

8. The method of claim 5, further comprising rinsing the treated assembly with water.

9. A method of forming a sensor, comprising:
   disposing an electrolyte between an in intimate contact with a first electrode and a second electrode to form an assembly, wherein the first electrode comprises a up to about 5 wt % rhodium and up to about 99.5 wt % platinum, based upon the weight of the first electrode;
   heating the assembly; and exposing the heated assembly to an alkaline solution selected from the group consisting of potassium hydroxide and barium hydroxide.

10. The method of claim 9, wherein the first electrode further comprises up to about 99 wt % of the metal and up to about 10 wt % metal oxide based upon the weight of the first electrode.

11. The method of claim 10, wherein the first electrode comprises about 94 wt % to about 99 wt % metal and about 1 wt % to about 6 wt % metal oxide.

12. The method of claim 11, wherein the metal oxide is alumina.

13. The method of claim 9, wherein said assembly is treated by immersing said assembly in an alkaline solution.

14. The method of claim 13, further comprising coating at least a portion of the assembly with a protective coating.

15. The method of claim 14, wherein the protective coating is combined with the alkaline solution.

16. The method of claim 15, wherein the alkaline solution is boiled.

17. The method of claim 15, wherein the sensor has a rich to lean response time of less than about 65 ms.

18. The method of claim 17, wherein the sensor has a rich to lean response time of less than about 60 ms.

19. The method of claim 9, further comprising disposing a heater in thermal communication with the electrolyte.

20. A method of forming a sensor, comprising:

disposing an electrolyte between an in intimate contact with a first electrode and a second electrode to form an assembly, wherein the first electrode comprises a up to about 5 wt % rhodium and up to about 99.5 wt % platinum, based upon the weight of the first electrode;

heating th e assembly; and exposing the heated assembly to barium hydroxide.

21. A method of forming a sensor, comprising:

forming an electrolyte;

densifying the electrolyte;

exposing the electrolyte to barium hydroxide; and disposing the electrolyte between and in intimate contact with a first electrode and a second electrode to form an assembly.

* * * * *